(12) United States Patent
Simons et al.

(10) Patent No.: US 11,712,367 B2
(45) Date of Patent: Aug. 1, 2023

(54) DEVICE AND SYSTEM FOR PERSONALIZED SKIN TREATMENT FOR HOME USE

(71) Applicant: KONINKLIJKE PHILIPS N.V., Eindhoven (NL)

(72) Inventors: Evelyn Josefina Maria Simons, Eersel (NL); Martin Jurna, Den Bosch (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 418 days.

(21) Appl. No.: 16/956,624

(22) PCT Filed: Dec. 19, 2018

(86) PCT No.: PCT/EP2018/085716
§ 371 (c)(1),
(2) Date: Jun. 22, 2020

(87) PCT Pub. No.: WO2019/121833
PCT Pub. Date: Jun. 27, 2019

(65) Prior Publication Data
US 2020/0397611 A1    Dec. 24, 2020

(30) Foreign Application Priority Data

Dec. 22, 2017  (EP) ..................... 17209990

(51) Int. Cl.
*A61N 1/40*    (2006.01)
*A61F 7/00*    (2006.01)
(Continued)

(52) U.S. Cl.
CPC .............. *A61F 7/00* (2013.01); *A61N 1/403* (2013.01); *A61N 5/0616* (2013.01);
(Continued)

(58) Field of Classification Search
CPC ................ A61F 7/00; A61F 2007/0003; A61F 2007/0075; A61F 2007/0093;
(Continued)

(56) References Cited

U.S. PATENT DOCUMENTS

2010/0191314 A1    7/2010  Young
2013/0274841 A1   10/2013  Eckhous
(Continued)

FOREIGN PATENT DOCUMENTS

DE   102014108315 A1   12/2015
ES       1042977 U     10/1999
(Continued)

OTHER PUBLICATIONS

International Search Report and Written Opinion dated Jan. 25, 2019 for International Application No. PCT/EP2018/085716 filed Dec. 19, 2018.
(Continued)

*Primary Examiner* — Ankit D Tejani
*Assistant Examiner* — Joshua Brendon Solomon

(57) ABSTRACT

The present invention relates to a mask-shaped skin treatment device and system. The device comprises one or more coupling agent detectors configured to detect presence of coupling agent on one or more skin portions of a user and one or more heating elements configured to cause local heating of one or more skin portions of the user. The one or more heating elements are configured to cause heat selectively based on the presence of coupling agent measured by the one or more coupling agent detectors.

20 Claims, 6 Drawing Sheets

(51) Int. Cl.
*A61N 5/06* (2006.01)
*A61F 7/02* (2006.01)
*A61N 1/08* (2006.01)
*A61N 5/067* (2006.01)

(52) U.S. Cl.
CPC .... *A61N 5/0625* (2013.01); *A61F 2007/0003* (2013.01); *A61F 2007/0075* (2013.01); *A61F 2007/0093* (2013.01); *A61F 2007/0096* (2013.01); *A61F 2007/0225* (2013.01); *A61F 2007/0228* (2013.01); *A61N 5/067* (2021.08); *A61N 2001/083* (2013.01); *A61N 2005/0647* (2013.01); *A61N 2005/0651* (2013.01); *A61N 2005/0659* (2013.01); *A61N 2005/0662* (2013.01)

(58) Field of Classification Search
CPC ...... A61F 2007/0096; A61F 2007/0225; A61F 2007/0228; A61N 1/403; A61N 5/0616; A61N 5/0625; A61N 5/067; A61N 2001/083; A61N 2005/0647; A61N 2005/0651; A61N 2005/0659; A61N 2005/0662
See application file for complete search history.

(56) References Cited

U.S. PATENT DOCUMENTS

| | | |
|---|---|---|
| 2016/0089536 A1 | 3/2016 | Mohammadi |
| 2018/0352937 A1* | 12/2018 | Vandier ................. A61B 5/6803 |
| 2021/0204996 A1* | 7/2021 | Ko ..................... A61B 18/1477 |

FOREIGN PATENT DOCUMENTS

| | | | |
|---|---|---|---|
| JP | S63216813 | 9/1988 | |
| JP | 2015164489 | 9/2015 | |
| JP | 2018187364 A | 11/2018 | |
| WO | 2009132606 A1 | 11/2009 | |
| WO | 2017037352 A1 | 3/2017 | |
| WO | WO-2018182188 A1 * | 10/2018 | ......... A61B 18/1206 |

OTHER PUBLICATIONS

International Preliminary Report on Patentability dated Oct. 11, 2019 for International Application No. PCT/EP2018/085716 filed Dec. 19, 2018.

* cited by examiner

DEVICE AND SYSTEM FOR PERSONALIZED SKIN TREATMENT FOR HOME USE

CROSS REFERENCE TO RELATED APPLICATIONS

This application is the U.S. National Phase application under 35 U.S.C. § 371 of International Application No. PCT/EP2018/085716 filed Dec. 19, 2018, published as WO 2019/121833 on Jun. 27, 2019. which claims the benefit of European Patent Application Number 17209990.5 filed Dec. 22, 2017. These applications are hereby incorporated by reference herein.

FIELD OF THE INVENTION

The present invention relates to a mask-shaped skin treatment device providing personalized heat-based skin treatment for home use. The present invention further relates to a system incorporating the aforementioned device.

BACKGROUND OF THE INVENTION

Skin tightening or firming is a popular cosmetic procedure because it addresses the visible signs of skin aging, including wrinkles and sagging skin. In general, a form of energy (e.g. radio frequency (RF), contact heating, optical energy) is applied to the skin and converted to thermal energy within the skin to raise locally the temperature of the skin. The main target is the dermis and depending on the level of increase in temperature, thermal effects can vary from fibroblast activation, increased collagen production to denaturation and contraction of collagen.

As a result of a mild thermal impact (40° C. to 45° C.) to the dermis, fibroblast stimulation occurs resulting in collagen remodeling. At higher thermal impact (50° C. to 90° C.) immediate collagen contraction occurs in the dermis followed by collagen remodeling through a controlled wound healing response over time with associated neocollagenesis. Several skin treatment devices based on especially RF-heating are presently available. Although professional and home-use skin treatment devices show high efficacy based on clinical studies, in the home-use situation it is difficult for the user to obtain similar results as shown by strictly guided/instructed claim validation tests.

In fact, numerous skin rejuvenation masks using light emitting diodes (LEDs), copper oxide, plant collagen, steam or vibration are commercially available with costs ranging between 30 $ and 2500 $. However, these masks provide full facial treatment such that treatment times are usually longer than needed to achieve the desired rejuvenation effect. Other home-use devices are handheld devices that heavily relay on the user's execution of treatment and hence the treatment outcome.

WO 2017/037352 A1 discloses a system for analysis and activation and/or active and localized release comprising a mask for applying to at least part of the face of the user, provided with at least one device for analyzing the skin of the face and at least one means for the active and localized release of dermo-cosmetic formulations from at least one storage means.

SUMMARY OF THE INVENTION

It is an object of the present invention to provide a home-use skin treatment device that allows for personalized skin treatment tailored to the needs of different skin types and skin portions and a treatment time that is as short as possible.

In a first aspect of the present invention a mask-shaped skin treatment device is presented that comprises
one or more coupling agent detectors configured to detect presence of coupling agent on one or more skin portions of a user, and
one or more heating elements configured to cause local heating of one or more skin portions of the user,
wherein the one or more heating elements are configured to cause heat selectively based on the presence of coupling agent measured by the one or more coupling agent detectors.

In a further aspect of the present invention, a skin treatment system is presented comprising
a mask-shaped skin treatment device according to claims 1 to 12, and
a control unit configured to control the one or more heating elements according to a predefined treatment program and/or according to user instructions.

Preferred embodiments of the invention are defined in the dependent claims. It shall be understood that the claimed system has similar and/or identical preferred embodiments as the claimed device, in particular as defined in the dependent claims and as disclosed herein.

The present invention is based on the idea to provide a skin treatment device for use at home offering personalized, skin-tailored treatment with a treatment time being as short as possible.

Currently available skin treatment devices are usually designed for facial skin. Said devices are either designed for full-face treatment or to cover only parts of a user's face. In any case mask-covered skin parts are heated even if there is no intention for treatment. None of these masks gives the opportunity to treat areas that the only consumer wants to treat. Hence, since more parts may be treated than required, the overall treatment time is longer than actually necessary.

Although there also exist smaller, hand-held treatment devices allowing for more selective skin treatment, application of such devices is more cumbersome. In particular, hand-held devices prevent the user from pursuing other activities during skin treatment.

The mask-shaped skin treatment device according to the present invention solves these problems. The present invention offers a skin treatment mask whose heating impact can be guided by coupling agent applied to the skin according to preferences of the user. In particular, skin areas of the user are only treated, i.e. affected by heat of the heating elements, if they are covered by the coupling agent. More specifically, the heat caused by the heating elements is adapted to the detection results of respective coupling agent detectors. This way, the heat by the one or more heating elements is applied selectively on the user's skin based on the presence of coupling agent. In case there exists only one heating element, said heat may only produce heat if coupling agent is detected to be present on the skin. If no coupling agent is detected, however, the heating element may not heat the skin. Therefore, also a single heating element may cause heat in a selective manner.

The coupling agent used may be any one of emulsion, cream, oil, fluid, paste or gel, in particular radio frequency conductive gel. In general, the coupling agent may be configured to change a feature of skin. In particular, the coupling agent may influence the moisture content of the skin and, more particularly, may be configured to increase the moisture content of the skin. However, the coupling agent may likewise influence the refelectivity or colour of the skin. Preferably, the coupling agent is thermally and electrically conductive. Furthermore, the coupling agent should be skin tolerant.

The ratio between heating elements and coupling agent detectors within the device may vary depending on the skin area to be treated. For example, device parts or devices used to treat skin around eyes may exhibit less heating elements than coupling agent detectors. Hence, skin temperature in such body regions may be controlled in a closely mashed way to protect the skin. Furthermore, the distance between heating elements and coupling agent detectors may be low in such device areas or devices to ensure that heat is precisely caused in those areas where desired and not anywhere else. On the other hand, device parts or devices used for less sensitive skin may exhibit more heating elements than coupling agent detectors.

Concerning the temperature provided by the one or more heating elements it should be noted that there exist numerous research papers available showing positive stimulation at temperatures between approximately 40 to 45° C. and times from seconds, minutes and even up to hours. The general trend is that having a higher temperature requires a shorter exposure time, and having a lower temperature requires a longer exposure time. The right combination provides the right thermal dosage that allows for an effective skin rejuvenation. Preferably, the heating elements cause a temperature between 40 and 45° C. in the user's skin.

Besides, the heating elements advantageously have a size between 1 to 5 $cm^2$, in particular between 2 to 3 $cm^2$. As experiments have shown, users experience the mentioned size range as the most comfortable. Still, the smaller the heating elements and coupling agent detectors are, the more precise may be treatment with the device because skin areas to be treated can be restricted with high precision. Hence even smaller heating elements are conceivable.

In an embodiment of the device, the one or more coupling agent detectors are configured to detect the presence of coupling agent by measuring impedance, in particular radio-frequency impedance, and/or conductance of the skin of the user. Application of coupling agent to the skin leads to an enhancement of skin moisture and accordingly to a decrease of the skin's impedance and an increase of the conductance, respectively. Hence, a change in skin impedance and/or conductance may indicate the presence of coupling agent on the skin. In other words, impedance and/or conductance are indicative for presence of coupling agent on the skin. Therefore, skin parts covered by coupling agent may be distinguished from parts without application of coupling agent. Accordingly, these parts may be treated separately from other skin parts. In order to gather a meaningful impedance and/or conductance measurement it is essential that the coupling agent used is conductive. However, a skin moisture measurement may also be based on near-infrared spectroscopy, preferably in the spectral range from 1300 to 2000 nm. Skin moisture may likewise be measured by a sensor configured to measure transepidermal water loss or by other known types of skin hydration sensors.

There are also other types of coupling agent detectors conceivable. In fact the presence of coupling agent on the skin may be measured by a (non-contact) optical detector configured to measure optical features which may comprise colour and/or reflectivity, for example. In fact, presence of coupling agent on the skin may not only influence the skin moisture but also the reflectivity and/or colour of the skin. Hence, skin regions with coupling agent applied may be distinguished from other skin regions by their reflectivity and/or colour. An optical detector may comprise a camera, for example.

In general, from a feature measured by the coupling agent detector, such as the skin's reflectivity for example, the detector may be configured to draw conclusions about the presence of coupling agent.

In another embodiment of the device, the heating elements are configured to be activated simultaneously, sequentially, pair wise or according to another predefined pattern. Depending on the skin area to be treated the device may offer one or more customized treatment programs. If the mask-shaped device covers a user's face completely, and if the user has applied coupling agent everywhere in his face, for example, the heating elements on the left hand side of the mask may be operated in parallel with mirror-inverted heating elements on the right hand side. This allows for a uniform improvement of the user's skin condition. Furthermore, heating elements configured to cover more sensitive skin areas may be operated with interruptions to prevent from skin irritations.

In a further embodiment, the one or more coupling agent detectors of the device are integrated in the one or more heating elements and/or placed outside the heating elements. Coupling agent detectors placed directly within the heating elements may reflect the presence or absence of coupling agent at the location of the heating elements in a reliable manner. Hence, heating elements with integrated coupling agent detectors may be controlled in a very precise and effective manner. Therefore, heating elements with integrated coupling agent detectors may be used, e.g. in such areas of the mask which are configured to be applied to sensitive skin areas. If not integrated in the heating elements the coupling agent detectors are preferably placed in the vicinity of these elements, in particular adjacent or directly adjacent to said elements.

In another embodiment of the skin treatment device, the one or more heating elements are configured to cause local heating of the one or more skin portions if the impedance measured by one or more corresponding coupling agent detector is below a predefined lower impedance threshold and/or above a predefined upper impedance threshold and/or if the conductance measured by a corresponding coupling agent detector is below a predefined lower conductance threshold and/or above a predefined upper conductance threshold.

If impedance is above a particular threshold and/or if conductance is below a particular threshold this may indicate that there is no or too little coupling agent applied to the user's skin. Correspondingly, heating elements associated with the corresponding skin areas advantageously lower the temperature they cause in the skin or are deactivated. Hence, skin burn and other irritations of the skin caused by heat can be prevented. On the other hand, a too low impedance (or a too high) conductance may indicate that the device is misused, i.e. applied to wet areas such as mucous membranes, eyes or lips. Therefore, if the coupling agent detectors indicate that the skin impedance is below a predefined threshold and/or if conductance is above a predefined threshold, the heating elements may also stop heating or at least lower the temperature they cause in the user's skin. In fact, the heating elements may be configured to heat the skin only if the impedance and/or conductance measured is within a predefined range. The thresholds and range mentioned may be adjustable.

In a further embodiment of the skin treatment device, the lower and/or upper impedance and/or conductance threshold are configured to be adapted to the skin type and or body area of the user. Impedance, in particular RF impedance, is dependent on the region of skin where impedance is measured. The same applies to conductance. The forehead skin of a person, for example, could exhibits a higher impedance than the skin of for example the cheeks. Thus, given a uniform distribution of coupling agent on the user's face, the forehead of a user may be treated with higher temperature than his/her cheeks. Furthermore, the impedance and/or conductance thresholds may be dependent on the RF electrode configuration used in the coupling agent detectors. In fact, skin impedance values are lower when a centrosymmetric electrode configuration is used rather than a stripe electron configuration.

In an embodiment of the device, the one or more heating elements are any one of contact heating elements, absorption-based heating elements and electrically-based heating elements. Contact heating elements are Peltier-based heating elements, for example. Under absorption-based heating elements lasers or light emitting diodes (LEDs) are understood. Further suited for skin treatment are Intense Pulsed Light (IPL) systems. Electrically-based heating elements may be radio frequency elements, for example. Unlike lasers, the RF technology produces electric current which generates heat through resistance in the dermis and as deep as subcutaneous fat.

In another embodiment, the device is configured to cover the face of the user completely or in parts and/or to cover other body parts and/or wherein the device is configured to be adapted to a body part contour of the user.

Usually, different users have different problem zones. If a user suffers from periorbital wrinkles or perioral wrinkles, for example, there is no need that the device covers his/her face completely. In such a case it suffices when the device is configured to only cover the eye area or mouth area. Although of all skin areas facial skin is the most exposed to environmental influences and hence usually requires the most care, there is a trend to treat other skin areas as well. In fact, consumers increasingly focus on treating the skin of neck and hands as well. Hence, the mask-shaped skin treatment device may also be configured to treat said areas.

Apart from that, the mask-shaped skin treatment device may be adapted to a body part contour of the user. For instance, the mask can be configured to be adapted to the shape of the face. The mask may either be provided in a pre-formed manner or formable such that the user may adapt the device form to desired body parts. An adapted mask shape ensures that the distance between heating elements and skin is the approximately the same for all heating elements. In turn, this allows for a uniform treatment result. In particular, the device may be made from flexible material to adapt to the user's skin like a second skin.

In another embodiment the mask-shaped skin treatment device further comprises one or more temperature sensors configured to measure the skin temperature of the user, wherein the one or more heating elements are further configured to adapt the heat they cause selectively based on the temperature measured by the one or more temperature sensors. Additional temperature sensors offer the possibility to further control the heating elements.

For example, if the heating elements induce a particular heat in the user's skin based on the measurements of the coupling detectors but said temperature is too high and causes skin burn, the temperature sensors detecting said temperature may transmit corresponding data to one or more associated heating elements in order to stop heating or at least to lower the temperature they cause in the skin. Apart from security or health aspects, temperature sensory may also be used for wellness reasons. For example, the temperature sensors may be used to measure the skin temperature continuously and if a predefined comfort temperature is exceeded the heating elements may be instructed to lower the temperature they cause in the user's skin. Likewise, there may be defined a temperature threshold which the heating elements may not fall below. Temperature may either be measured continuously or with interruptions of a predefined length.

The one or more temperature sensors may be any one of thermistors, thermocouples, resistance temperature detectors, infrared sensors and semiconductor sensors. Above all, thermistors are highly sensitive sensors, low in cost and small in size such that they may fit into the smallest spaces, in particular inside the heating elements.

In yet another embodiment, the one or more temperature sensors of the skin treatment device are integrated in the heating elements and/or placed outside the heating elements. Temperature sensors placed directly within the heating elements are highly sensitive to temperature changes induced by the respective elements. Hence, heating elements with integrated temperature sensors may be controlled in a very precise and effective manner. Therefore, these heating elements are preferably used in such areas of the mask which are to be applied to sensitive skin areas. If not integrated in the heating elements the temperature sensors are preferably placed in the vicinity of these elements, in particular adjacent or directly adjacent to said elements.

In an advantageous embodiment, the mask-shaped skin treatment device further comprises one or more light elements configured to stimulate photobiomodulation of the skin.

In this embodiment, the skin treatment results are further improved. The one or more light elements used may be anyone of lasers, light emitting diodes (LEDs), and broadband light in the visible and near infrared spectrum. The light sources are placed near to or in contact with the skin, allowing the light energy, i.e. photons, to penetrate skin tissue. Consequently, chromophores located in cells of the skin are interacted with resulting in photo physical and photochemical changes that lead to alterations at the molecular, cellular and tissue levels of the body. In particular, wound healing and regeneration of diseased and damaged tissue is accelerated, inflammations are reduced and acute and chronic pain is reduced. Apart from that light may generally enhance performance in normal tissues and accelerate cell cycles resulting in rejuvenation of the skin.

In another embodiment, the mask-shaped skin treatment device comprises one or more fixation elements configured to fix the device on the skin of the user. On the one hand fixation of the device allows for controlled skin treatment because relocations of the device on the skin are prevented. On the other hand there is no need for the user to hold the device. Thus, the user could do a different activity during treatment (e.g. watching TV, cooking or other house related activities). Accordingly, the suggested device offers skin firming and rejuvenation in an effective and comfortable manner. Fixation elements may be any one of straps, elastic bands, temples, adhesive and other appropriate means.

In an embodiment, the device further comprises a control unit configured to control the one or more heating elements according to a predefined treatment program and/or according to user instructions, and/or a user interface configured to obtain user instructions from the user and/or to convey information about any one of heating element temperature, skin impedance, skin conductance and treatment program, in particular treatment duration.

The predefined treatment program may either be provided by the mask-shaped skin treatment device itself or by the user via the user interface. For example, if the device is configured to treat the lower eye region only, the heating elements may be controlled according to a pre-stored program in every treatment session. If, however, the device is configured to be used for the whole face and to treat dullness, sagging, laxity and pigmentation spots in addition to wrinkles the user must have the opportunity to choose between different programs or to compose a treatment program of his own. Accordingly, the user interface may be used by the user to transmit the desired treatment program. The user interface may be touchscreen, for example, where the user can enter his/her desired maximum comfort temperature, program duration etc. The user interface may also be a display informing the user about the current treatment program. Likewise, the user may be informed about treatment beginning and ending via an acoustic signal.

In an embodiment of the skin treatment system, the system further comprising a user interface configured to obtain user instructions from the user and/or to convey information about any one of heating element temperature, skin impedance, skin conductance and treatment program, in particular treatment duration. The user interface of the system may be a smartphone, for example, wherein the heating element temperature and treatment duration are displayed on the smartphone's display.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
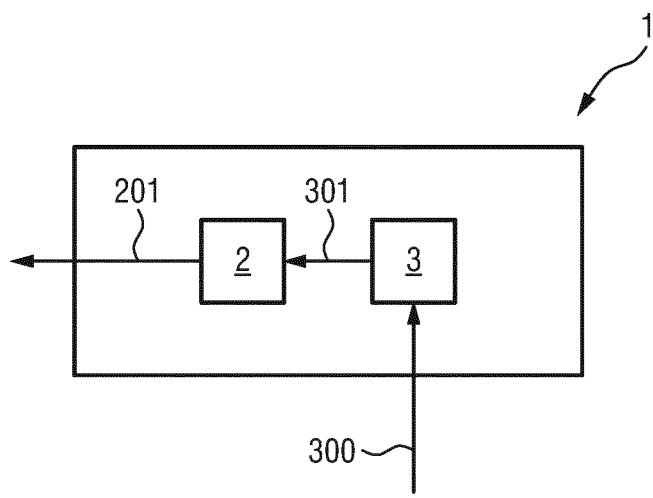
FIG. 1 shows a schematic diagram of a first embodiment of a mask-shaped skin treatment device according to the present invention.

FIG. 1 shows a schematic diagram of a first embodiment of a mask-shaped skin treatment device 1 according to the present invention. The mask-shaped skin treatment device 1 comprises a heating element 2 and a coupling agent detector 3.

The heating element 2 of this embodiment is Peltier elements having a size of 3 cm$^2$. If the coupling agent detector 3 detects a coupling agent signal 300 exceeding a predefined signal threshold, the detector 3 transmits the corresponding coupling agent data 301 to the heating element 2. Based upon the data 301 obtained the heating element 2 causes heat 201 in the skin of the user by contact heating. During heating, coupling agent may vaporize. In this embodiment, since the coupling agent detector 3 is configured to detect coupling agent continuously, the amount of coupling agent detected decreases over time. If the amount of coupling agent detected falls below a first predefined threshold, the heating element 2 lowers the temperature induced in the skin of the user. If the amount of coupling agent detected decreases further and falls below a second predefined threshold below the first predefined threshold, the heating element 2 stops heating.

Figure 2:
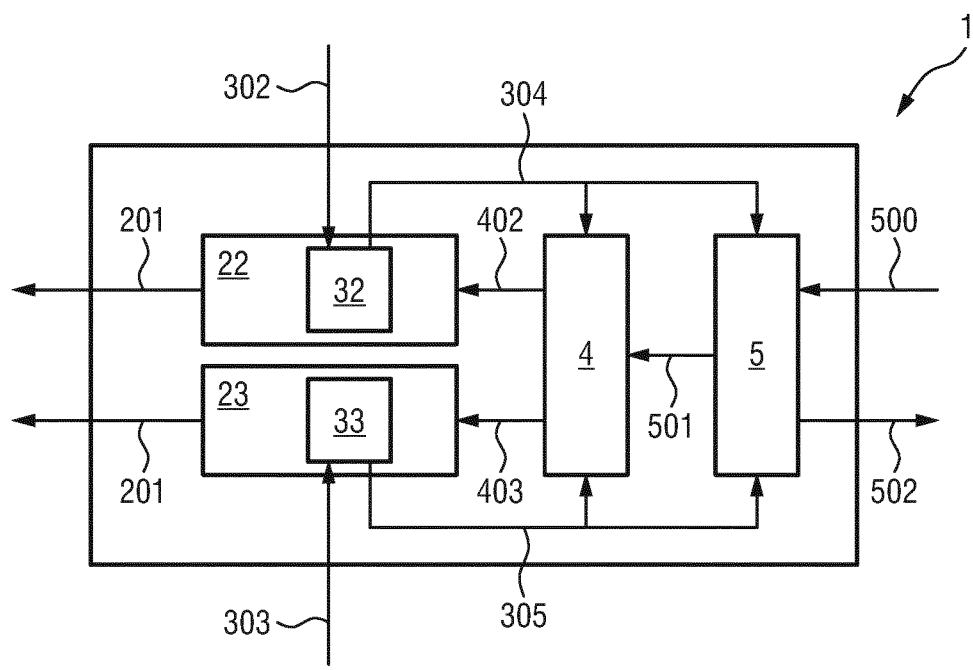
FIG. 2 shows a schematic diagram of a second embodiment of a mask-shaped skin treatment device according to the present invention.

FIG. 2 shows a schematic diagram of a second embodiment of a mask-shaped skin treatment device 1 according to the present invention. Apart from two heating elements 22 and 23 and two coupling agent detectors 32 and 33 each integrated in of the heating elements 22 and 23, respectively, this embodiment comprises a control unit 4 configured to control the two heating elements and a user interface 5.

Using the user interface 5, the user may choose between several treatment programs including, for example, a wrinkle treatment program suited for wrinkle treatment or a program for primarily relaxation. Having received the corresponding user instructions 500, the user interface 5 transmits the corresponding instruction data 501 to the control unit 4. Subsequently, the control unit 4 transmits control signals 402 and 403 to control the heating elements 22 and 23 according to said instructions data 501. Accordingly, the heat 201 of the heating elements 22 and 23 induced in the skin of the user conforms with the user instructions 500.

To ensure that the heating elements 22 and 23 only cause heat in those skin areas the user wishes to treat, the coupling agent detectors 32 and 33 detect whether the user has applied (enough) coupling agent on respective skin areas or not. In particular, the coupling agent detectors 32 and 33 are configured to detect coupling agent signals 302 and 303 indicating the amount, if any, of coupling agent on the skin. The corresponding coupling agent data 304 and 305 are then transmitted to the control unit 4, which is configured to control the heating elements 22 and 23 in accordance. If the amount of coupling agent detected by any one of the coupling agent detectors 32 and 33 is below a predefined threshold, the control unit 4 is configured to transmit a control signal 402 and/or 403 to the respective heating element(s). For example, if the amount of coupling agent detected by coupling agent detector 32 is above a predefined threshold associated with said detector 32, the control unit 4 instructs the corresponding heating element 22 to stop heating. However, since heating element 23 may be configured to be used on different skin areas than heating element 22, the threshold regarding the amount of coupling agent on the skin may be higher for heating element 23. Therefore, if the coupling agent detector 33 detects the same amount of coupling agent at detector 23, the control unit does not instruct the heating element 23 to stop heating. In fact, heating element 23 may further induce heat in the user's skin.

The detection results 304 and 305 of each detector are furthermore transmitted to the user interface, which presents the data 304 and 305 as user information 502 to the user.

Hence, the user is given the opportunity to control whether he/she has applied (enough) contact agent to skin areas he/she wishes to be treated.

Figure 3:
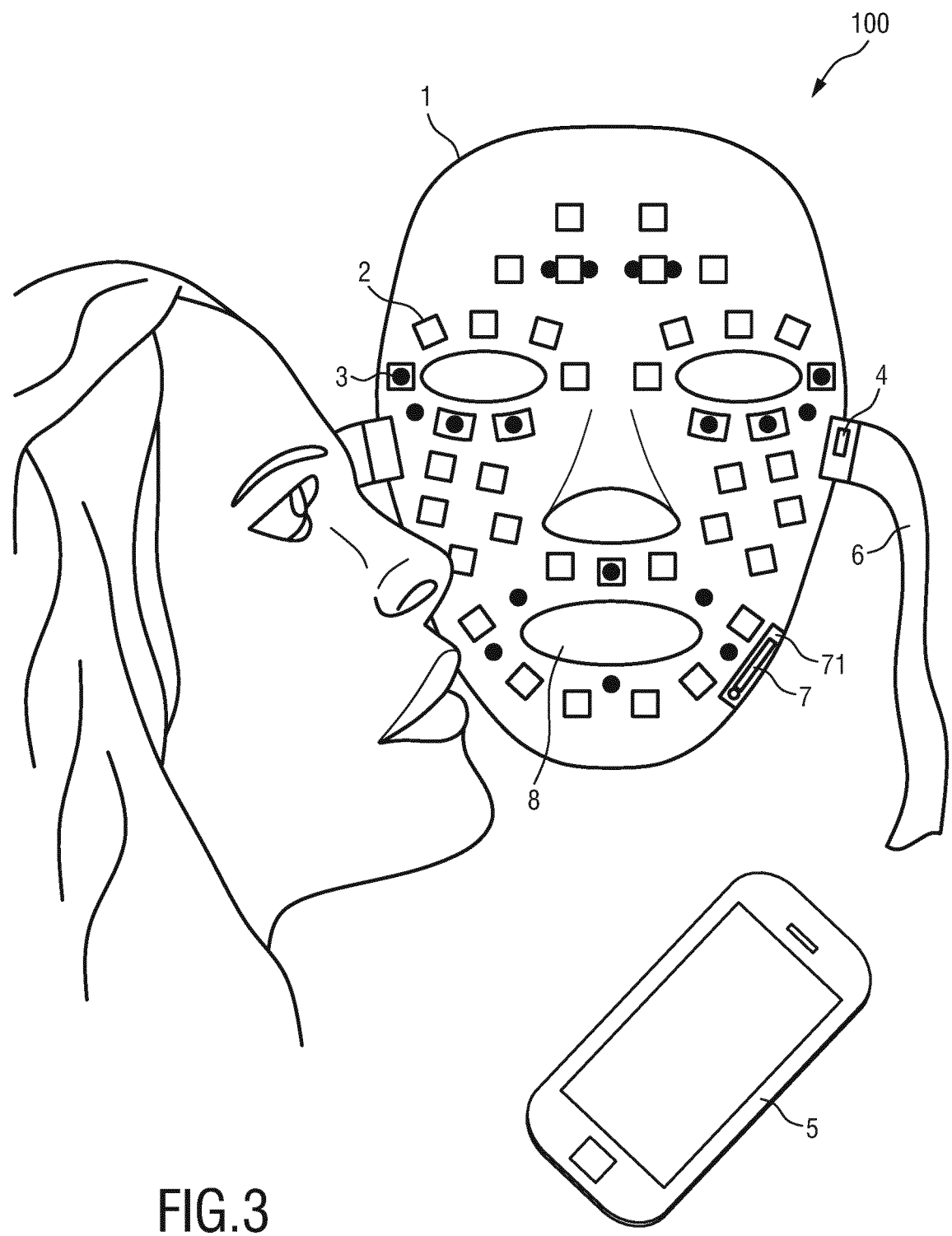
FIG. 3 shows a side view of an exemplary implementation of a first embodiment of a mask-shaped skin treatment system according to the present invention.

FIG. 3 shows a side view of an exemplary implementation of a first embodiment of a mask-shaped skin treatment system 100 according to the present invention. The system 100 comprises an embodiment of a mask-shaped skin treatment device 1 configured as full-face mask and a user interface 5 in the form of a smartphone. The mask 1 comprises multiple heating elements 2 and coupling agent detectors 3. In addition, the mask comprises a control unit 4 and a lashing strap as fixation element 6. The heating elements 2, coupling detectors 3 and control unit 4 are operated by a battery 7 comprised within a battery compartment 71. To enhance user comfort the mask 1 further comprises holes 8 for eyes, nose and mouth.

The heating elements 2 in this embodiment are rectangular Peltier elements providing contact heat to the skin. The number of coupling agent detectors 3 varies among different mask areas. Mask areas to be applied to more sensitive skin areas are covered by more coupling agent detectors 3 than areas corresponding to less sensitive skin areas. Hence, the area applied to the forehead and around the eyes and mouth is covered by more coupling agent detectors 3 than the mask area used for the cheeks, for example. For more precise measurements, coupling agent detectors 3 used to measure the skin temperature in more sensitive skin areas are integrated in the heating elements 2 while other coupling agent detectors 3 are placed outside the heating elements 2. The control unit 4 controlling the heating elements 2 is configured to receive user instructions via the user interface 5. In this embodiment, the control unit 4 may receive said information wirelessly.

Figure 4:
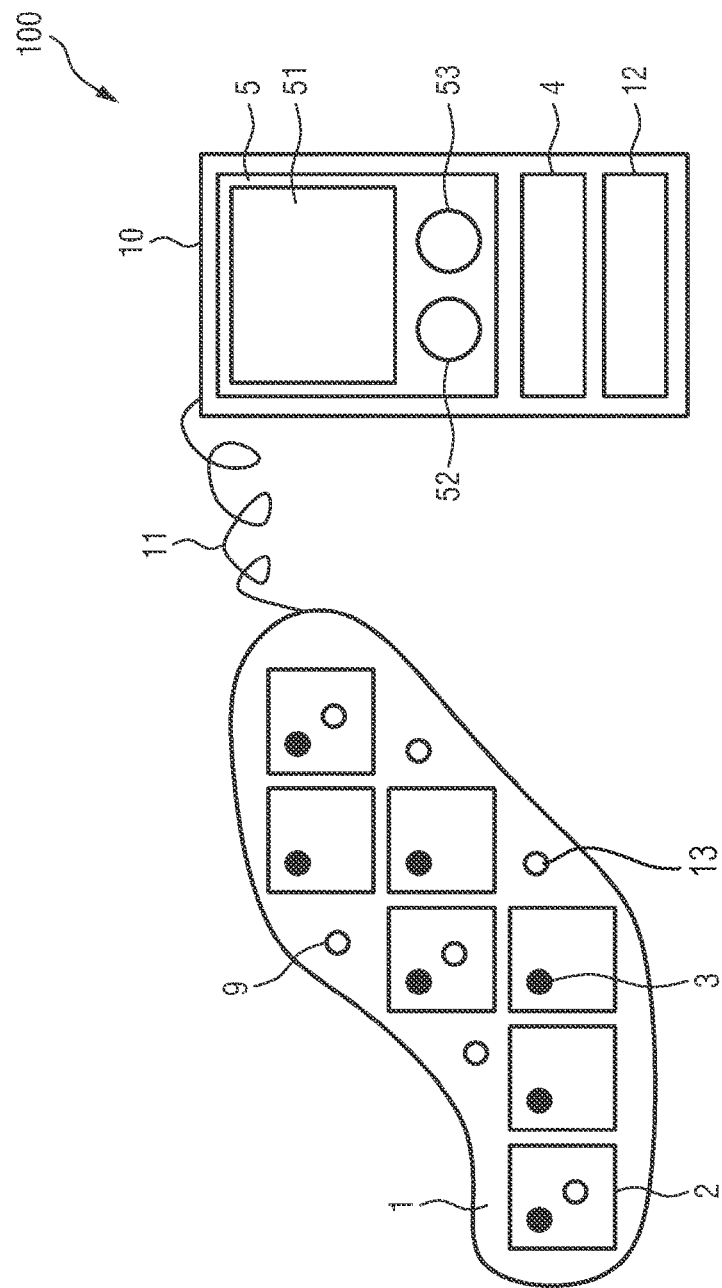
FIG. 4 shows a top view of an exemplary implementation of a second embodiment of a mask-shaped skin treatment system according to the present invention.

FIG. 4 shows a top view of an exemplary implementation of a second embodiment of a mask-shaped skin treatment system 100 according to the present invention. This embodiment of a mask-shaped treatment system 100 is represented by a patch 1, comprising several heating elements 2, coupling agent detectors 3, temperature sensors 9 and light elements 13 connected via a cable 11 to a base station 10 comprising a user interface 5, a control unit 4 and a storage unit 12. The user interface 5 comprises a display 51 and two selection buttons 52 and 53.

This embodiment is configured to provide skin treatment using thermal and photobiomodulation effects in the human skin. Light elements 13 and heating elements 2 may be activated simultaneously, sequentially or according to a predefined program. Predefined programs for the individual operation of heating elements 2 and light elements 13 or their collaboration may be stored in the storage unit 12. The programs available may be displayed on the display of the base station 10 and the user may choose a particular program using the selection buttons 52 and 53. Upon selection of a program the control unit 4 may control the temperature caused by the heating elements and the light emitted by the one or more light elements 13 in accordance with said program. In particular, the control unit 4 controls the intensity of light provided by the light elements. However, the control unit 4 may likewise control the wavelength at which the light elements are operating. Furthermore, using the user interface 5, the user may indicate a maximum comfortable temperature which he/she wishes not to be exceeded by the heating elements 2.

The mask-shaped skin treatment device 1 is given by a flexible patch comprising adhesive and hence may be attached to any region of the user's body. Furthermore, the base station 10 is configured to be small enough to be stored in a trouser pocket of the user. Hence the user may even do sports during treatment.

Figure 5C:
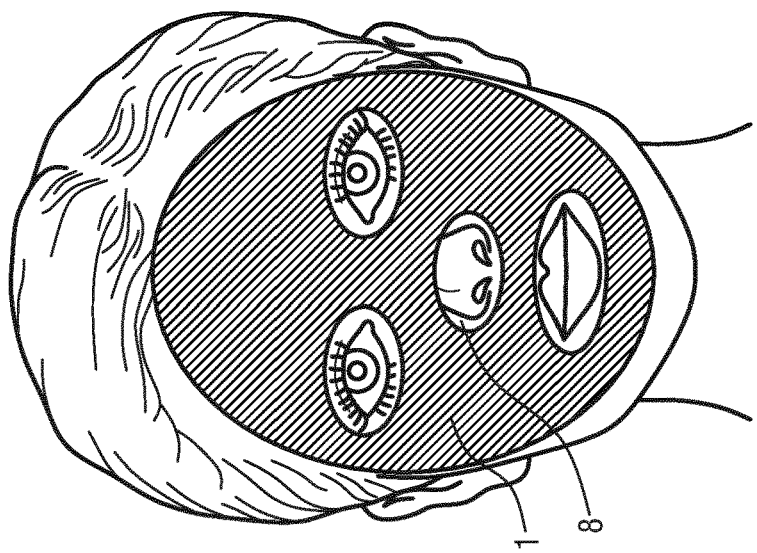
FIGS. 5A, 5B and 5C show each a front view of an exemplary implementation of an embodiment of a mask-shaped skin treatment device.
Figure 5B:
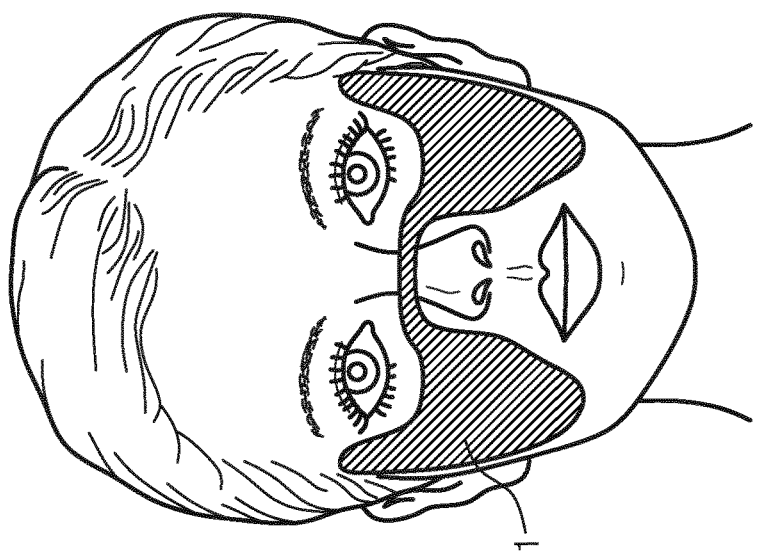
Figure 5A:
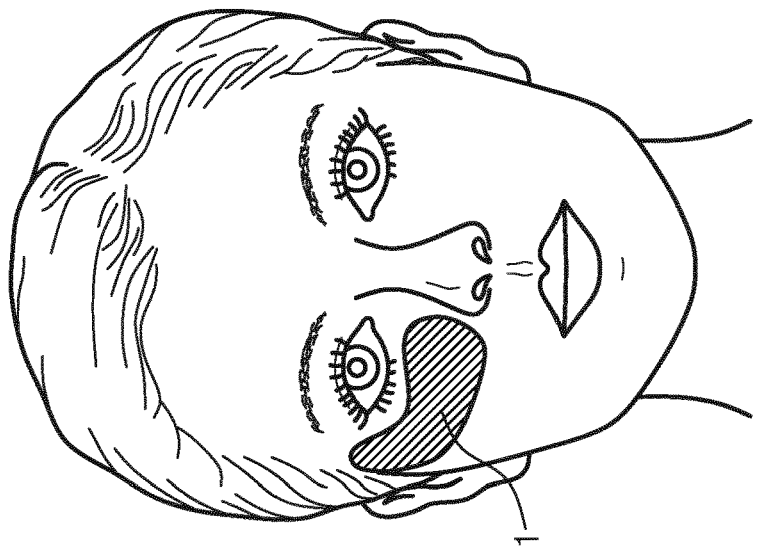

FIGS. 5A, 5B and 5C show each a front view of an exemplary implementation of an embodiment of a mask-shaped skin treatment device 1. While FIG. 5A shows an embodiment of a device 1 that solely covers the lower eye region of the user, FIG. 5B shows an embodiment that covers both cheeks and FIG. 5C shows an embodiment which covers the face of the user completely apart from his/her eyes, nose and mouth. The embodiment solely covering the lower eye region is particularly suited for skin rejuvenation below the eyes and to treat periorbital wrinkles. With the embodiment shown in FIG. 5B, wrinkles on cheeks may be treated effectively. The mask 1 as shown in FIG. 5C offers a full-face treatment. Holes 8 inside the mask increase user comfort.

Figure 6:
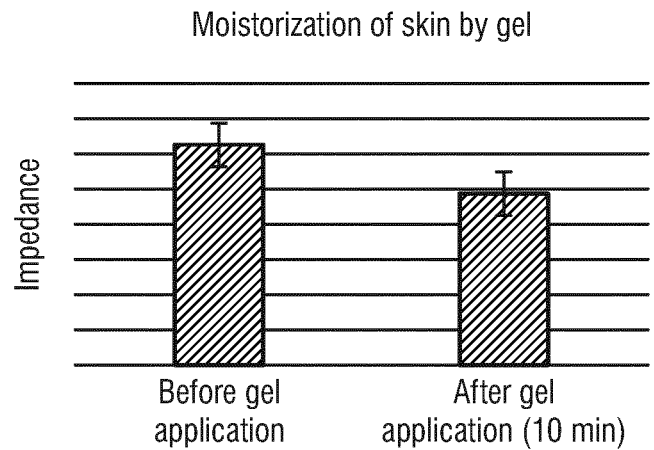
FIG. 6 shows the relationship between moisturization of skin by gel and skin impedance.

FIG. 6 shows the relationship between moisturization of skin by gel and skin impedance. In particular, the impact of gel on skin impedance is shown by comparing the levels of skin impedance prior to gel application and ten minutes after gel application. As can be seen there is a significant decrease of skin impedance after the application of gel as coupling agent. Indeed, gel enhances the skin moisture level and hence leads to a decrease of impedance in the user's skin. The application of gel as coupling agent may therefore indicate the presence or absence and also the amount of gel on the user's skin.

Figure 7:
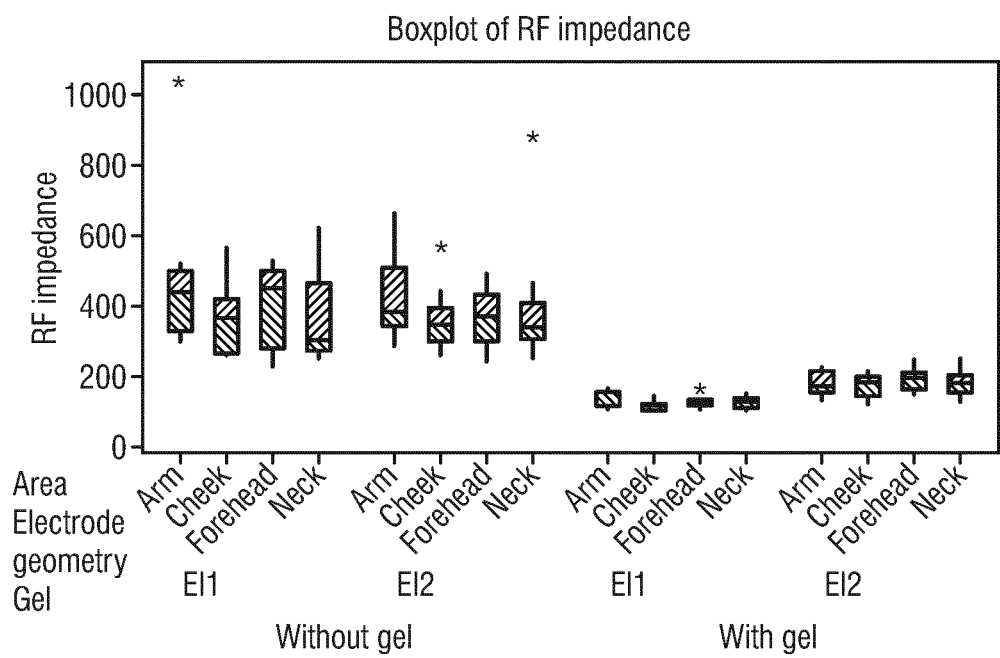
FIG. 7 shows the relationship between RF impedance for skin of several body parts with respect to electrode geometry and application of gel on the skin.

FIG. 7 shows the relationship between RF impedance (in Ohm) for skin of several body parts with respect to electrode geometry and application of gel on the skin. Irrespective of the electrode type used to measure skin impedance, there is a significant difference in impedance of the skin if gel is applied or not. In fact, skin with gel applied on its surface exhibits a significantly lower skin impedance than skin without any gel application. Although skin corresponding to different body areas exhibit different levels of impedance, this matter of fact is also independent of the body area.

Generally, there is always a range of impedance associated with a particular RF frequency, which is due to the initial moisturization level of the skin in combination with the gel and the inter person variation and body location. In addition, the RF frequency will slightly change the measured impedance. The range decreases by the application of gel due to the fact the interpersonal differences (moister level, dry skin, flaky skin, moisturized skin) will be replaced by a full moisturization of the skin for all by the gel.

Figure 8A:
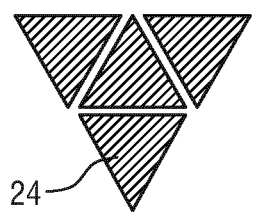
FIGS. 8A, 8B and 8C show different embodiments of heating elements according to the present invention.
Figure 8B:
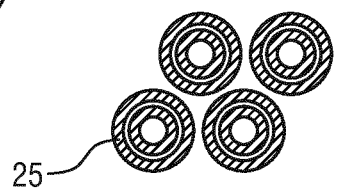
Figure 8C:
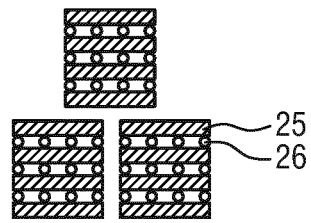

FIGS. 8A, 8B and 8C show different embodiments of heating elements 2 according to the present invention. FIG. 8A shows four triangular-shaped Peltier heating elements 24. FIG. 8B shows a radio frequency configuration, in particular four centrosymmetric radio frequency electrodes 25. FIG. 8C shows a squared heating element created from different line shaped radio frequency electrodes 25, where in between the electrodes 25 LEDs 26 are located. The LEDs 26 may either be used for inducing heat or to provide an additional photobiomodulation effect.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A mask-shaped skin treatment device, comprising:
   one or more coupling agent detectors configured to detect presence of coupling agent previously applied on corresponding one or more skin portions of skin of a user by measuring at least one of impedance or conductance of the skin of the user; and
   one or more heating elements configured to cause selective local heating of the one or more skin portions of the user where the one or more coupling agent detectors detect the presence of the coupling agent,
   wherein the one or more heating elements are configured to cause the selective local heating by applying heat to the one or more skin portions when the impedance measured by the one or more corresponding coupling agent detectors is below a predefined impedance threshold or when the conductance measured by the one or more corresponding coupling agent detectors is above a predefined conductance threshold.

2. The mask-shaped skin treatment device according to claim 1, wherein the one or more heating elements are configured to be activated simultaneously, sequentially, pair wise or according to another predefined pattern.

3. The mask-shaped skin treatment device according to claim 1, wherein the one or more coupling agent detectors are integrated in the one or more heating elements, respectively.

4. The mask-shaped skin treatment device according to claim 1, wherein the predefined impedance threshold is adapted to at least one of a skin type or a body area of the user.

5. The mask-shaped skin treatment device according to claim 1, wherein the one or more heating elements are any one of contact heating elements, absorption-based heating elements and electrically-based heating elements.

6. The mask-shaped skin treatment device according to claim 1, further comprising a mask portion configured to cover at least a portion of a face of the user.

7. The mask-shaped skin treatment device according to claim 1, further comprising one or more temperature sensors configured to measure skin temperature of the skin of the user, wherein the one or more heating elements are further configured to cause the selective local heating of the one or more skin portions of the user based on the skin temperature measured by the one or more temperature sensors.

8. The mask-shaped skin treatment device according to claim 7, wherein the one or more temperature sensors are integrated in the heating elements.

9. The mask-shaped skin treatment device according to claim 1, further comprising one or more light elements configured to stimulate photobiomodulation of the skin.

10. The mask-shaped skin treatment device according to claim 1, further comprising one or more fixation elements configured to fix the device on the skin of the user.

11. The mask-shaped skin treatment device according to claim 1, further comprising:
    a control unit configured to control the one or more heating elements according to at least one of a predefined treatment program or user instructions; and
    a user interface configured to obtain user instructions from the user and to convey information about one or more of heating element temperature, skin impedance, skin conductance and treatment duration.

12. A skin treatment system comprising:
    the mask-shaped skin treatment device according to claim 1; and
    a control unit configured to control the one or more heating elements according to a least one of a predefined treatment program or according to user instructions.

13. The skin treatment system according to claim 12, further comprising:
    a user interface configured to obtain user instructions from the user and to convey information about one or more of heating element temperature, skin impedance, skin conductance and treatment duration.

14. The mask-shaped skin treatment device according to claim 1, wherein the one or more coupling agent detectors are placed outside the one or more heating elements, respectively.

15. The mask-shaped skin treatment device according to claim 1, wherein the predefined conductance threshold is adapted to at least one of a skin type or a body area of the user.

16. The mask-shaped skin treatment device according to claim 7, wherein the one or more temperature sensors are placed outside the heating elements.

17. A skin treatment device, comprising:
    a mask configured to fit over a face of a user;
    a plurality of coupling agent detectors arranged on the mask and configured to detect presence of coupling agent previously applied on a corresponding plurality of skin portions of skin of the user by measuring at least one of impedance or conductance of the skin of the user, wherein the presence of the coupling agent decreases impedance and increases conductance of the skin of the user; and
    a plurality of heating elements arranged on the mask and configured to cause selective local heating of the plurality of skin portions of the user based on the presence of the coupling agent detected by the plurality of coupling agent detectors, wherein the plurality of heating elements cause the selective local heating by applying heat to each skin portion of the plurality of skin portions having impedance below a predefined impedance threshold or having conductance above a predefined conductance threshold.

18. The skin treatment device of claim 17, wherein the plurality of heating elements further cause the selective local heating by removing heat from each skin portion of the plurality of skin portions having an impedance above the predefined impedance threshold or having a conductance below the predefined conductance threshold.

19. The skin treatment device of claim 17, further comprising:
    at least one temperature sensor configured to measure skin temperature of the skin of the user, wherein the plurality of heating elements are further configured to cause the selective local heating of the plurality of skin portions of the user based on the skin temperature measured by the one or more temperature sensors.

20. A mask-shaped skin treatment device, comprising:

a plurality of coupling agent detectors configured to detect presence of coupling agent previously applied on a corresponding plurality of skin portions of skin of a user by measuring at least one of impedance or conductance of the skin of the user;

a plurality of heating elements configured to apply local heating to the plurality of skin portions of the user, respectively; and a control unit configured to cause the plurality of heating elements to selectively heat one or more skin portions of the plurality of skin portions having impedance below a predefined impedance threshold or having conductance above a predefined conductance threshold.

\* \* \* \* \*